US010842987B2

(12) United States Patent
Kramer et al.

(10) Patent No.: US 10,842,987 B2
(45) Date of Patent: Nov. 24, 2020

(54) TUBE CLAMP AND VOLUMETRIC PUMP COMPRISING TUBE CLAMP

(71) Applicant: B. BRAUN MELSUNGEN AG, Melsungen (DE)

(72) Inventors: Matthias Kramer, Melsungen (DE); Sarah Jacobskötter, Kiel (DE); Jürgen Steger, Körle (DE); Helmut Freigang, Körle (DE); Christian Schrödl, Stuttgart (DE); Stefan Batzdorf, Fulda (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 174 days.

(21) Appl. No.: 16/125,044

(22) Filed: Sep. 7, 2018

(65) Prior Publication Data
US 2019/0091463 A1    Mar. 28, 2019

(30) Foreign Application Priority Data
Sep. 28, 2017   (DE) .......................... 10 2017 122 647

(51) Int. Cl.
*A61M 39/28*    (2006.01)
*A61M 5/168*    (2006.01)
*A61M 5/142*    (2006.01)

(52) U.S. Cl.
CPC .......... *A61M 39/286* (2013.01); *A61M 5/142* (2013.01); *A61M 5/16813* (2013.01); *A61M 39/284* (2013.01); *A61M 2205/3334* (2013.01)

(58) Field of Classification Search
CPC ............ A61M 39/286; A61M 5/16813; A61M 5/142; A61M 39/284; A61M 2205/3334; A61M 39/28; A61M 2025/024
See application file for complete search history.

(56) References Cited

U.S. PATENT DOCUMENTS

2008/0141498 A1    6/2008 Ruffing
2010/0268161 A1    10/2010 Traversaz
(Continued)

FOREIGN PATENT DOCUMENTS

DE    102013014217 A1    2/2015
DE    102014018164 A1    6/2016
(Continued)

OTHER PUBLICATIONS

Extended European Search Report for European Application No. 18 193 774.9, dated Jan. 24, 2019, with translation, 12 pages.
(Continued)

*Primary Examiner* — Amber R Stiles

(57) ABSTRACT

A medical tube clamp for clamping a flexible medical tube comprising: a tube receiving area which is adapted to receive the medical tube, a first clamping portion including a first clamping jaw which is movable relative to a second clamping portion including a second clamping jaw, and a closure system for safely positioning the two clamping portions in more than one snap-fit position relative to each other so that, when the closure system is unlocked, the medical tube can be inserted in and removed from the tube clamp, in an open snap-fit position the inserted medical tube cannot be removed and is not clamped and in a clamping snap-fit position the medical tube is clamped between the first clamping jaw and the second clamping jaw, with the first clamping jaw being configured to be elastically movable relative to the first clamping portion via a connecting member and/or the second clamping jaw being configured to be elastically movable relative to the second clamping portion via a connecting member. In addition, the invention relates to a volumetric pump.

11 Claims, 5 Drawing Sheets

(56) References Cited

U.S. PATENT DOCUMENTS

2014/0336613 A1* 11/2014 Roth .................... A61M 39/28
                                                    604/500
2017/0120040 A1*  5/2017 Burkholz ............ A61M 39/288
2017/0312427 A1  11/2017 Steger et al.

FOREIGN PATENT DOCUMENTS

| DE | 102015117493 A1 | 4/2017 |
| EP | 2183016 A1 | 5/2010 |
| EP | 2583716 A1 | 4/2013 |
| GB | 2439325 A | 12/2007 |
| WO | 2006081866 A1 | 8/2006 |

OTHER PUBLICATIONS

German Search Report for German Application No. 10 2017 122 647.8, dated Apr. 5, 2018, with English translation—11 pages.

* cited by examiner

TUBE CLAMP AND VOLUMETRIC PUMP COMPRISING TUBE CLAMP

CROSS REFERENCE TO RELATED APPLICATIONS

This application claims priority to German Patent Application No. DE 10,2017/122,647.8 filed Sep. 28, 2017, the contents of such application being incorporated by reference herein.

FIELD OF THE INVENTION

The present invention relates to a medical tube clamp, especially an infusion tube clamp, for (sealingly) clamping and, respectively, pinching off a flexible medical tube, especially an infusion tube specifically for use in an infusion pump, comprising a tube receiving area adapted to receive the medical tube, a first clamping portion (upper shell) including a first clamping jaw which is movable relative to a second clamping portion (lower shell) including a second clamping jaw, and a closure system for safely positioning the two clamping portions in more than one snap-fit position relative to each other so that in an unlocked inserting position of the two clamping portions the medical tube and, respectively, a tube portion hereof (without any further changes required at one tube end, for example without previous disconnection from an active agent reservoir so as to push the tube through an opening) can be inserted in and removed from the tube clamp in the tube receiving area thereof, in a (locked) open snap-fit position the inserted medical tube cannot be removed and is not clamped and in a (locked) clamping snap-fit position the medical tube is (sealingly) pinched (off)/squeezed/clamped between the first clamping jaw and the second clamping jaw. In addition, the invention relates to a volumetric pump according to the preamble of the independent claim.

DESCRIPTION OF THE RELATED ART

From the state of the art, diverse tube clamps and infusion tube pumps are known. Usually these are displacement pumps which from outside displace a volume in a flexible tube (single-use article) and thus avoid contamination of the pump mimics with the medium guided inside the tube. In the field of infusion technology, it is of immanent importance that a tube establishing a connection between a patient and an active agent reservoir must never be opened without the flow rate being checked, as otherwise an uncontrolled quantity of active agent might be fed to the patient in a so-called "free-flow situation". In afore-mentioned pumps it is therefore necessary to interrupt the flow through the single-use article, when the pump is opened, for example for replacing the single-use article. For this purpose, usually it is prescribed to the user (e.g. via a signal output on a display of the infusion pump) to manually close a safety clamp/tube clamp/infusion tube clamp, e.g. a roller clamp, prior to opening the pump. In the event that the user forgets to close the safety clamp or does not correctly close the safety clamp, a free-flow situation endangering the patient will occur.

From EP 2 583 716 B1 a generic infusion tube clamp/tube clamp/clamp for insertion into an infusion pump is known, for example. Said clamp includes a base comprising an infusion pump receiving area as well as a first clamping leg and a second clamping leg for squeezing an infusion tube, the two clamping legs being pivotally connected to each other at a first infusion tube clamp end. Via a snap-fit unit/snap-fit closure system the two clamping legs may be safely positioned at more than one position relative to each other.

BACKGROUND OF THE INVENTION

In the state of the art, a problem will arise when the clamp is closed. From the continuously increasing pressing force with increasing swiveling and, respectively, closing of the two clamping legs toward each other in order to squeeze the tube, frequently high force and tension peaks are resulting. This causality inter alia is due to the fact that the medical tubes are not always configured to be exactly identical or different tubes with different geometric dimensions and moduli of elasticity can be used in the tube clamp. Also, it is difficult and cost-intensive to manufacture the tube clamp with constantly exactly identical tolerances. On the one hand, said force peak requires great effort of operating staff members for closing the tube clamp and moreover constitutes a high safety risk, as the snap-fit closure system will not completely snap fit in an unfavorable case and may inadvertently come loose again so that a dangerous "free-flow situation" may inadvertently occur. In addition, there are infusion pumps having tube clamps which automatically close the tube clamp via a pivoted door, which further impedes optical or acoustic check of safe snap fit of the closure system.

SUMMARY OF THE INVENTION

Therefore, it is an object of the invention to avoid or at least to alleviate the drawbacks from the state of the art and to provide ways and means for enabling an increase in the operating safety of a tube clamp as well as of a volumetric pump. A preferred objective of the present invention resides in rendering insertion and clamping of a flexible medical tube in a tube clamp and in a volumetric pump safer and easier.

Said objects and objectives are achieved according to aspects of the invention as regards a generic tube clamp by the feature that the first clamping jaw is formed/configured to be elastically/resiliently movable relative to the first clamping portion via a connecting member and/or the second clamping jaw is configured to be elastically/resiliently movable relative to the second clamping portion via a connecting member. In other words, the medical tube clamp is configured such, that the first clamping jaw is elastically/resiliently movable relative to the first clamping portion via a connecting member and/or the second clamping jaw is elastically/resiliently movable relative to the second clamping portion via a connecting member.

Basically, the present invention provides a (partial) uncoupling and, respectively, an elastically/resiliently movable coupling between the clamping portion and the clamping jaw via the connecting member. A constructional design of the tube clamp helps to realize the at least one connecting member which in the case of flux of force is connected in series between the first clamping jaw and the second clamping jaw. In this way, with an overall consideration of the flux of force, elasticity can be adjusted between the two clamping jaws, whereas the two clamping portions are configured to be rigid, when considered relative thereto, and primarily in combination with the closure system serve for safe positioning relative to each other. Such constructional design of the tube clamp helps to absorb especially force peaks and to safely fix the two clamping portions relative to each other.

The risk of inadvertent release of the positioning and, respectively, of the clamping snap-fit position is largely suppressed.

The tube clamp according to aspects of the invention facilitates, by the (partial) uncoupling and, respectively, elastic coupling of the clamping jaw and the clamping portion and thus the (partial) uncoupling of the closing mechanism (including the two clamping portions and the closure system) and the clamping mechanism (clamping jaws), the tube clamp to be completely locked and, respectively, brought into the clamping snap-fit position even more safely and easily with even more independence of the inserted medical tube and of the clamping mechanism.

Advantageous embodiments are claimed in the subclaims and shall be explained in the following.

Preferably, in the clamping snap-fit position the first clamping portion may be positioned by the closure system to be rigid/immobile/inelastic with respect to the second clamping portion, especially the two clamping portions are relatively rigid/inelastic due to a geometric design by a corresponding material (for example by a thick wall, by introduced braces or profiles in combination with a low modulus of elasticity), and the first clamping jaw and/or the second clamping jaw is/are elastically movable substantially only in a clamping pressure direction (direction in which the force of the clamping jaw acts on the inserted tube in the clamping snap-fit position). The elastic mobility of the clamping jaw with respect to the clamping portion merely in the clamping pressure direction (a translational degree of freedom) helps to absorb a tension peak during clamping, whereas an otherwise (intended) rigid connection of the clamping jaw to the clamping portion is maintained.

According to a preferred aspect, the two clamping portions of the tube clamp may be designed to be pivoting relative to each other. Especially, the tube clamp may include a hinge, especially preferred a film hinge, by which the first clamping portion is pivoting relative to the second clamping portion about a pivot axis so that the medical tube clamp can be opened and closed in a jaw-type/jaw-like manner. For example, the closure system can be arranged on the side opposed to the hinge. Advantageously, the respective clamping jaw of the respective clamping portion is arranged between the closure system and the pivot axis and, respectively, the hinge.

According to another aspect of the invention, the tube clamp may include, instead of the hinge, also a mechanism by which the second clamping portion has only a translational degree of freedom and is movable in the direction of the first clamping portion. Said translational movement of the two clamping portions toward or against each other is a further alternative embodiment apart from the pivoting movement.

In accordance with an advantageous development, the closure system may be in the form of a snap-fit closure system/snap-fit (having, besides an unlocked inserting position, two snap-fit positions). Such snap-fit closure system permits to easily and safely realize the two snap-fit positions of open snap-fit position and clamping snap-fit position of the tube clamp. Such snap-fit closure system is known from EP 2 583 716 B1 and its disclosure shall be fully incorporated and be part of the present application.

Preferably, the first clamping jaw and/or the second clamping jaw may be in the form of a clamping edge (having a linear geometric shape) the longitudinal axis (the longitudinal clamp axis/the longitudinal clamp direction) of which extends transversely to the longitudinal axis of the inserted medical tube (the longitudinal tube axis). Such clamping edge/clamping blade/clamping wedge is adapted to pinch off the medical tube in an optimally sealing manner without damaging the same.

According to a preferred embodiment, the first clamping portion and/or the second clamping portion may have a plate-shaped base which has at least one recess, especially in the form of a slotted hole, preferably in the area directly abutting on the respective clamping jaw, thus forming a connecting member in the base. Hence, by specifically introducing the recess, the connecting member can be integrally incorporated already in the clamping portion.

Of preference, the clamping jaws may be clamping edges having the longitudinal clamp direction and the first clamping portion and/or the second clamping portion may include two slotted holes whose longitudinal direction (of the slotted hole) is transverse to the longitudinal clamp direction and each slotted hole abuts preferably directly to the respective clamping edge. This arrangement of the slotted holes causes the clamping edge (as the clamping jaws) to be uncoupled or detached from the clamping portion on two sides, whereas the remaining two sides of the clamping edge remain connected to the clamping portion. Said two remaining connecting areas/connecting points constitute the two connecting members which render (each of) the respective clamping jaw elastically movable relative to its clamping portion. In particular, the elasticity can be adjusted by defining the thickness of the connecting members.

It is of advantage when the first clamping portion, the connecting member and the first clamping jaw are formed of one material (are one piece of material) and/or the second clamping portion, the connecting member and the second clamping jaw are formed of one material (are one piece of material). Especially preferred, the entire medical tube clamp including the hinge is formed of one material (is one piece of material). Especially preferred, the tube clamp may be made from synthetic material and, further preferred, may be configured as a (thermoplastic) injection-molded part made from one material in which both the connecting members and the hinge are integrally incorporated or, respectively, are formed by specific material recesses in a tube clamp wall surface.

Preferably, the connecting member may be an elastic material, a spring or a biasing mechanism. In said three different elements/embodiments a desired elasticity can be defined in different ways: by defining a specific modulus of elasticity, by choosing/changing a specific spring constant or by choosing a preload of the biasing mechanism that fit the requirements.

Another independently claimed aspect of the invention relates to a generic volumetric pump, especially an infusion pump, for delivering a medium through a flexible medical tube, comprising a housing, wherein, according to aspects of the invention, a medical tube clamp according to aspects of the invention is, preferably detachably, mounted on the housing for sealingly pinching (off) the medical tube. By using a medical tubing clamp according to aspects of the present invention, a safer and easier way of handling the volumetric pump can be achieved.

BRIEF DESCRIPTION OF THE DRAWINGS

The invention is best understood when read in connection with the accompanying drawings.

DETAILED DESCRIPTION OF PREFERRED EMBODIMENTS

Figure 1:
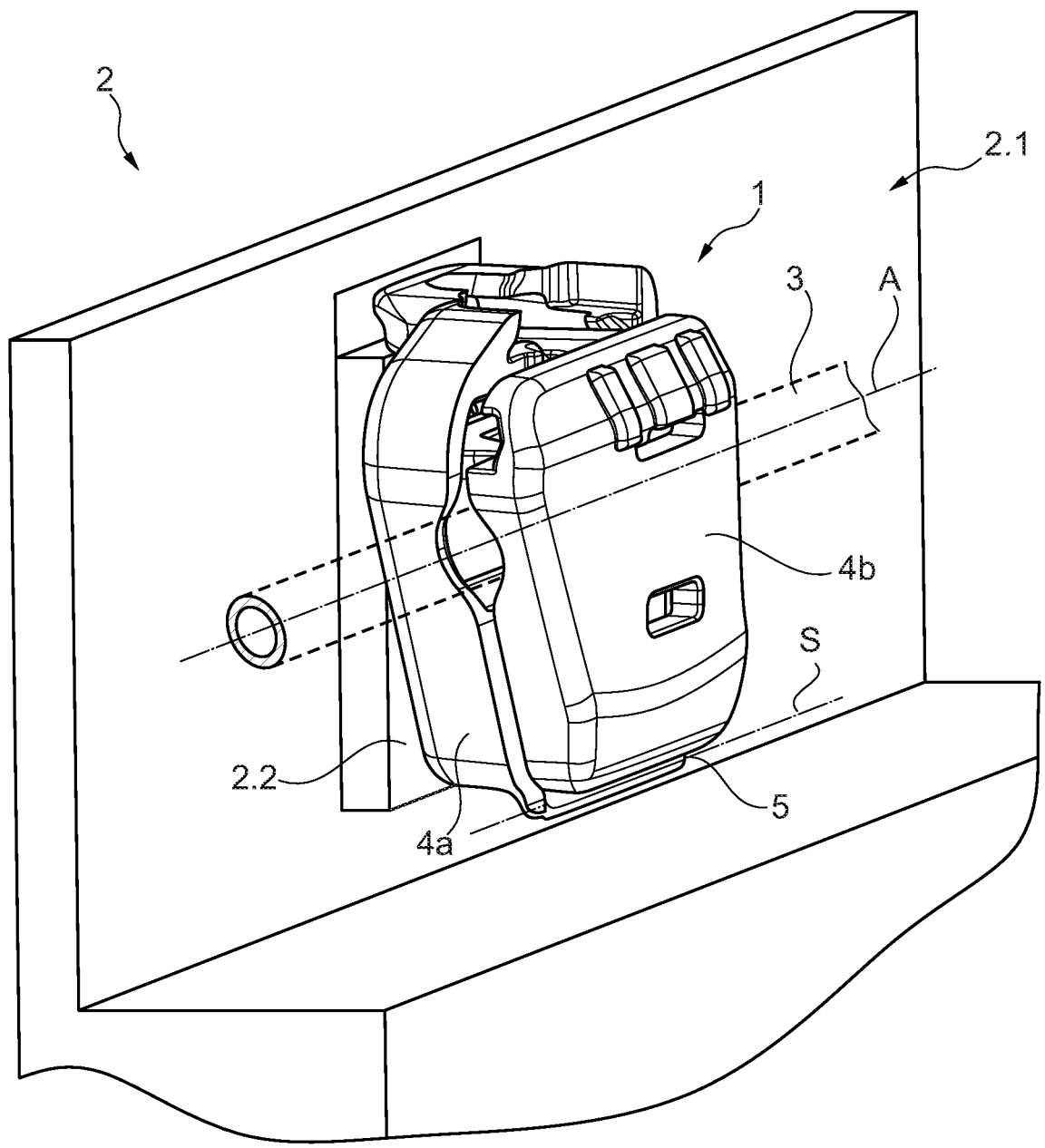
FIG. 1 shows a perspective view of a tube clamp according to aspects of the invention of a first preferred embodiment comprising an inserted medical tube, the tube clamp being inserted in a volumetric pump according to aspects of the invention of a first embodiment.

FIG. 1 schematically shows a perspective view of a medical tube clamp 1 according to aspects of the invention, more exactly speaking an infusion tube clamp 1 of a first preferred embodiment which is inserted in a volumetric pump 2 according to aspects of the invention in the form of an infusion pump 2 (here schematic partial view) with a dedicated housing 2.1. A flexible medical tube 3 (here schematic partial view) in the form of an infusion tube 3 is received in the infusion tube clamp 1 by clamping snap-fit (clamping snap-fit position). The schematically shown infusion pump 2 is a pump having a slide peristalsis in which the infusion tube 3 connecting a patient to an active agent reservoir (not shown) is placed upstream of the peristaltic slides (not shown) arranged in a tube insertion opening closable by a pump flap (not shown). The pump flap is subsequently closed and serves as a counter-bearing for the peristaltic slides pushing a volume inside the flexible infusion tube 3 in a defined delivery direction in a wave-shaped displacing motion.

In said medical tube clamps 1 as well as in said infusion pumps 2 the flexible infusion tube 3 in the form of a single-use article frequently has to be newly inserted or replaced. Such inserting/replacing operation is very complicated as the infusion tube 3 has to be positioned exactly upstream of the pump mimics (not shown) so that volume delivery can take place at all. It is the objective of the present invention inter alis to render the inserting/replacing operation of the infusion tube 3 easier and safer for the operating staff members, to assist correct insertion and safe snap-fit and, respectively, clamping of the infusion tube 3 by constructional measures and preferably to enable single-handed and gentle insertion/replacement of the tube. This objective is achieved by the tube clamp 1 according to aspects of the invention which shall be explained in detail in the following.

Figure 2:
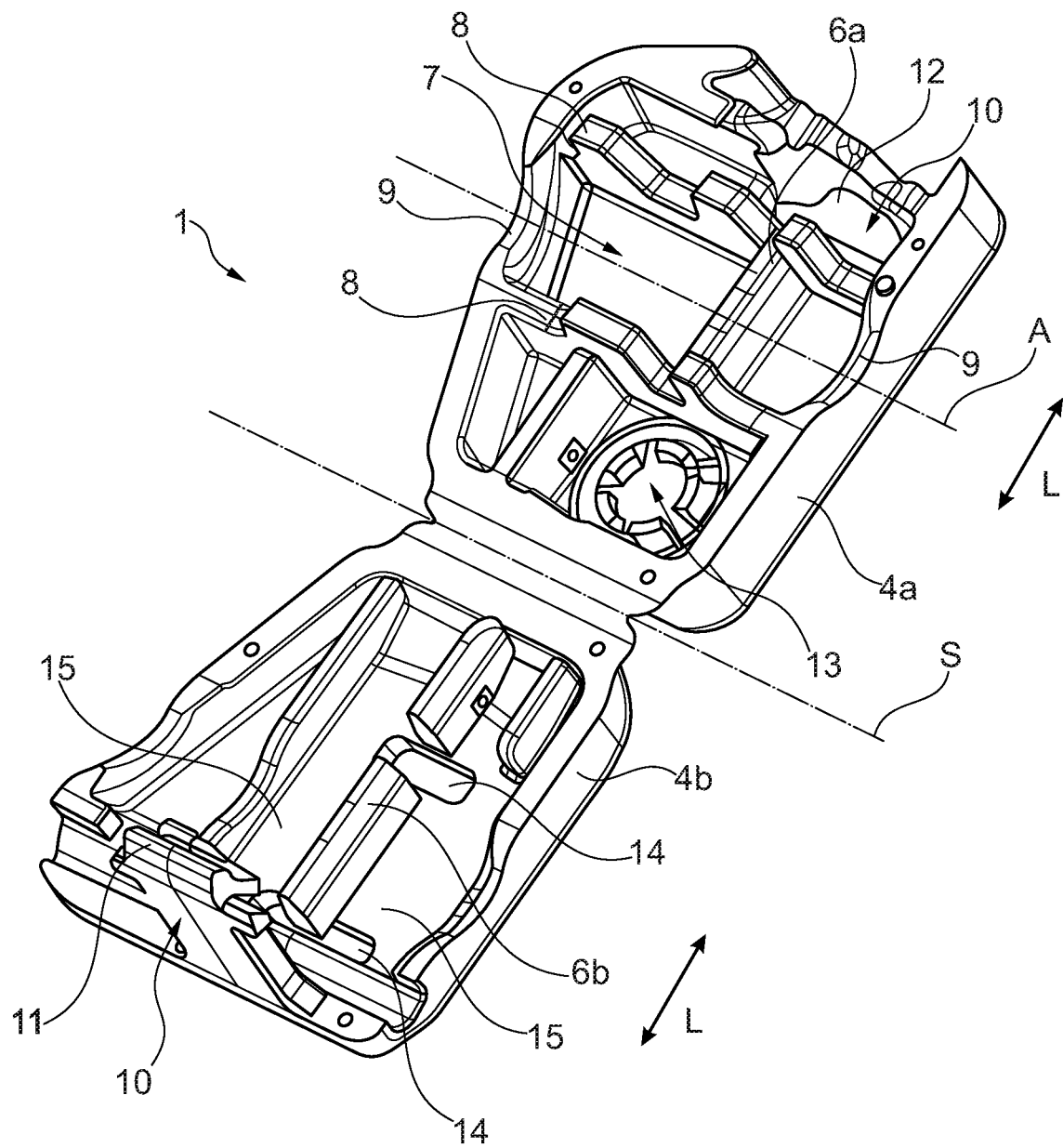
FIG. 2 shows a perspective view of the tube clamp of the first preferred embodiment in an unlocked inserting position in which the internal structure of the tube clamp is illustrated.
Figure 3:
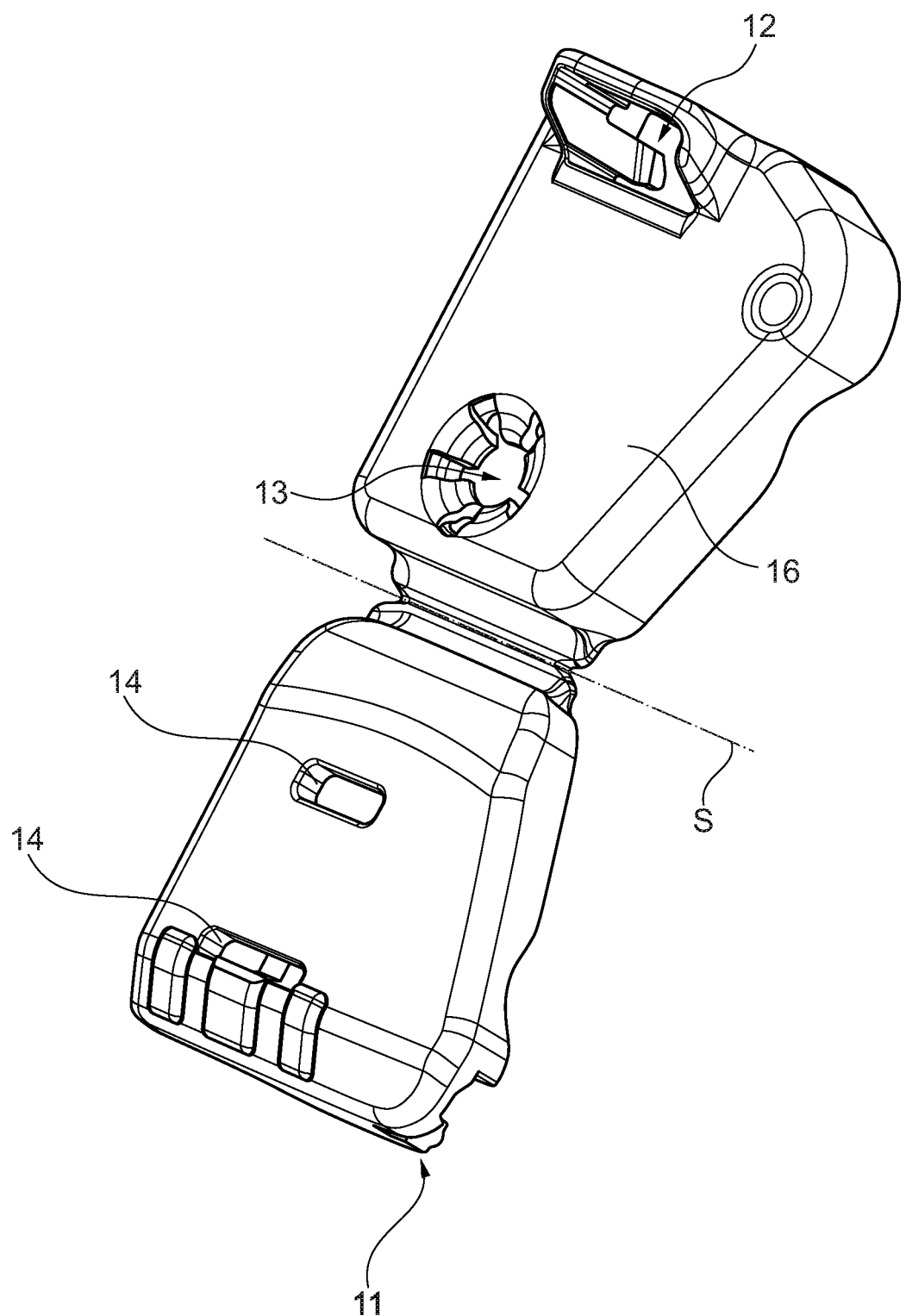
FIG. 3 shows a perspective view of the tube clamp of the first preferred embodiment in an unlocked inserting position in which the outer design of the tube clamp is illustrated.

FIGS. 2 to 6 show the tube clamp 1 of the first preferred embodiment. In FIGS. 2 and 3, the tube clamp 1 being in an unlocked inserting position is shown in greater detail. The tube clamp 1 includes a first clamping portion 4a and a second clamping portion 4b which can be pivoted against each other. To this end, the two clamping portions 4a, 4b are connected to each other at one end to be pivoting about a pivot axis S by a (film) hinge 5. Both clamping portions 4a, 4b can be manufactured, when advantageously being already connected to the hinge 5, from synthetic material as a single/one-material injection-molded part. Each of the first clamping portion 4a and the second clamping portion 4b includes a shell-type base having a trapezoid contour, with the trapezoid contour and, respectively, the outline of the first clamping portion 4a being formed symmetrically to the second clamping portion 4b so that the two clamping portions 4a, 4b in a clamping snap-fit position (see FIGS. 1 and 5), similar to a suitcase or a shell, form a uniform body (trapezoid in a top view).

The first clamping portion 4a includes a first clamping jaw 6a in the form of a clamping edge/clamping blade in a centrally located area of the trapezoid body (disposed between the hinge 5 and the opposite side). The clamping edge 6a protrudes perpendicularly from the first clamping portion 4a forming the first shell-type base of the tube clamp 1 in the direction of the second clamping portion 4b (in a clamping snap-fit position, cf. FIG. 1 and FIG. 5). The first clamping edge 6a is wall-shaped and extends linearly in a longitudinal clamp direction L which is transverse to the pivot axis S of the hinge 5. The second clamping portion 4b, too, has a second clamping jaw 6b in the form of a clamping edge in a centrally located area of its trapezoid body. Said second clamping edge 6b is wedge-shaped and extends in the clamping snap-fit position (see FIG. 1 and FIG. 5) equally linearly in the longitudinal clamp direction L and thus also transversely to the pivot axis S. The first clamping edge 6a and the second clamping edge 6b are formed at an equal distance from the pivot axis S and symmetrically regarding their expansion when viewed in the longitudinal clamp direction L. Since the two clamping edges 6a, 6b are also level with the pivot axis S, the two clamping edges 6a, 6b are moving or pivoting toward each other when the clamping portions 4a, 4b pivot/close, so as to clamp an infusion tube 3 therebetween.

The tube clamp 1 includes a tube receiving area 7 for receiving the infusion tube 3. More exactly speaking, in this embodiment the first clamping portion 4a includes the tube receiving area 7. To this end, when viewed in the longitudinal clamp direction L, at each of the ends of the first clamping edge 6a there is formed a land 8 including projections which extends in parallel to the pivot axis S and, respectively, perpendicularly to the longitudinal clamp direction L and which in the clamping snap-fit position projects from the first clamping portion 4a to the second clamping portion. Between said two lands 8 the infusion tube 3 can be inserted. The first clamping edge 6a (longitudinal clamp axis L) is transverse to a longitudinal tube axis A of the inserted infusion tube 3. In addition, at the passages of the infusion tube 3 inserted between the two lands 8 through the side faces of the first clamping portion 4a pitch-shaped recesses/openings/cutouts/pits 9 are provided so that the round infusion tube 3 will fit in the latter.

At the upper ends of the clamping portions 4a, 4b, when viewed in the longitudinal clamp direction L, which are facing away from the hinge 5 a closure system 10 in the form of a snap-fit closure system is arranged by which the tube clamp 1 realizes the two snap-fit positions, namely the open snap-fit position and the clamping snap-fit position. More exactly, the snap-fit closure system 10 includes a resilient snap hook 11 which, starting from an unlocked inserting position shown in FIG. 2, is deflected transversely to its longitudinal direction upon pivoting of the two clamping portions 4a, 4b toward each other in a closing direction via a run-on slope while overcoming its inherent material elasticity so as to then engage in a snap eye 12. Equally, the snap hook 11 can be released from said engagement while overcoming its inherent material elasticity so as to return or move the tube clamp 1 to the unlocked inserting position again. In the following, the snap-fit closure system 10 shall be described in detail with the aid of FIGS. 4 and 5.

The first clamping portion 4a moreover includes a press-button hole 13 adjacent to the film hinge 5 or, respectively, close to the pivot axis S so as to detachably mount the tube clamp 1 on the infusion pump 2 (see FIG. 1). The arrangement of the press-button hole 13 close to the pivot axis S is intended to inhibit or at least minimize inadvertent release of the tube clamp 1 when the tube clamp 1 is opened. In addition, the snap-fit closure system 10 is formed in the tube clamp 1 such that it forms a projection adapted to interact with a recess of the housing 2.1 so as to define an orientation of the tube clamp 1 rotatable about the press-button hole 13.

In contrast to the state of the art, in the second clamping portion 4b specifically two recesses 14 were introduced in the form of an elongate slit or in the form of a slotted hole which extend in parallel to the pivot axis S and, respectively, in parallel to the longitudinal tube axis A of the infusion tube 3 as well as transversely to the longitudinal clamp axis L. The two slotted holes 14 are approximately equal in length as to their dimensions in the direction transversely to the longitudinal clamp direction L and are symmetrically opposed to each other as regards the second clamping edge 6b. More exactly speaking, the two slotted holes 14 are introduced to the second clamping portion 4b directly adjacent to the two ends/sides of the second clamping edge 6b when viewed in the longitudinal clamp direction L. The structural design of said two slotted holes 13 causes the second clamping edge 6b to be uncoupled on two sides from the second clamping portion 4b and to be connected to the second clamping portion 4b only via two elastic connecting members or connectors or, respectively, connecting areas 15. Said elastic connecting members 15 cause the second clamping edge 6b to have a defined resilient mobility with respect to the rigidly formed second clamping portion 4b. More exactly, the second clamping edge 6b has structural elastic mobility in a clamping pressure direction D (in a clamping snap-fit position transversely to the second clamping portion 4b and transversely to the longitudinal tube axis A of the inserted infusion tube 3, see FIG. 1 and FIG. 5). The technical advantage resulting herefrom when pivoting the two clamping portions 4a, 4b against each other and, respectively, when closing and snap-fastening the tube clamp 1 shall be illustrated below with the aid of FIGS. 4 to 6.

FIG. 3 illustrates a further view of the tube clamp 1 of FIG. 2 in a perspective representation viewing the outer surface. The first clamping portion 4a includes a planar bearing face/bearing portion 16 which at the housing 2.1 of the infusion pump 2 rests or bears on a complementary planar counter-bearing surface 2.2 (see FIG. 1). The shown bearing surface 16 moreover serves to back the housing-side first clamping portion 4a so that, when closing (locking) the tube clamp 1 and pinching (off) an infusion tube 3 inserted in the tube receiving area 7, merely the second clamping portion has to be pivoted and pressed toward the housing 2.1 (see FIG. 1) until the snap-fit closure system 10 will engage and lock.

Figure 4:
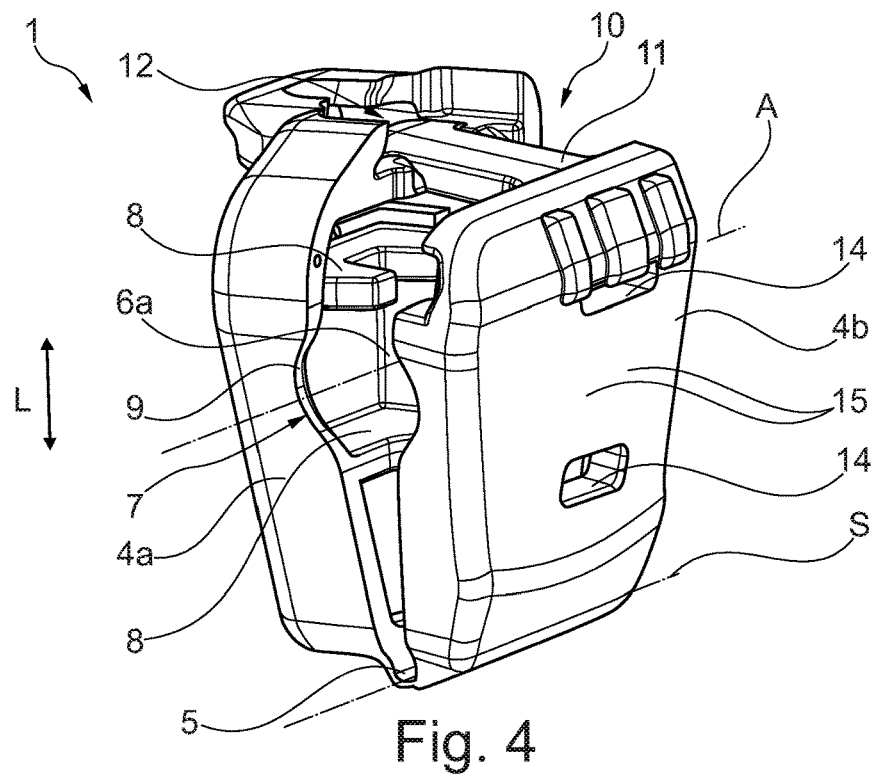
FIG. 4 shows a perspective view of the tube clamp of the first preferred embodiment in an open snap-fit position.

The functioning of the structurally designed elastic mobility of the second clamping edge 6b with respect to the second clamping portion 4b via the connecting member 15 shall be illustrated in the following. FIG. 4 shows the tube clamp 1 of FIG. 1 to FIG. 3 of the first preferred embodiment in the open snap-fit position. With respect to the unlocked inserting position of FIG. 2 and FIG. 3 in which both clamping portions 4a, 4b can pivot freely movably relative to each other about the pivot axis S and in which the infusion tube 3 can be inserted or removed, the two clamping portions 4a, 4b were pivoted toward each other in the closing direction and the snap hook 11 of the snap-fit closure system 10 was deflected via the run-on slope while overcoming its inherent material elasticity transversely to its longitudinal direction and, after that, in an intermediate position (open snap-fit position) snapped into the snap eye 12 (locked via undercut). In said open snap-fit position, the inserted infusion tube 3 (not shown here for reasons of clarity, rather cf. FIG. 1) is inserted in the tube receiving area so that it cannot be removed again without opening the snap-fit closure system 10, whereas the infusion tube 3 is not pinched, however (state of released flow of the fluid through the infusion tube 3).

When the second clamping portion 4b is further swiveled in the closing direction relative to the first clamping portion 4a, the two opposed clamping jaws 6a, 6b increasingly pinch off the flexible and elastic infusion tube 3 disposed therebetween. From a specifically defined pivot angle which is also dependent on the geometry and the material of the infusion tube 3, a flow through the infusion tube 3 is completely pinched off. The snap hook 11 of the snap-fit closure system 10 from a defined point engages in the first clamping portion 4a via undercut after overcoming another run-on slope and while overcoming its inherent elasticity and, in this way, safely pinches off the infusion tube 3 in the clamping snap-fit position. Due to the two slotted holes 14 introduced and the two connecting members 15 formed on both sides of the second clamping edge 6b, upon closing a force peak is reduced and safe locking of the snap-fit closure system is ensured, as the second clamping edge 6b is elastically movable relative to the second clamping portion 4b. Whereas a further relative movement in the clamping pressure direction D is hardly possible when the second clamping edge 6b directly bears on the already (completely) squeezed infusion tube 3, the second clamping portion 4b, on the other hand, may be further pressed against the first clamping portion 4a and can be safely locked in the clamping snap-fit position via the snap-fit closure system due to the (partial) uncoupling or serial connection/coupling via the elastic connecting members 15.

Figure 5:
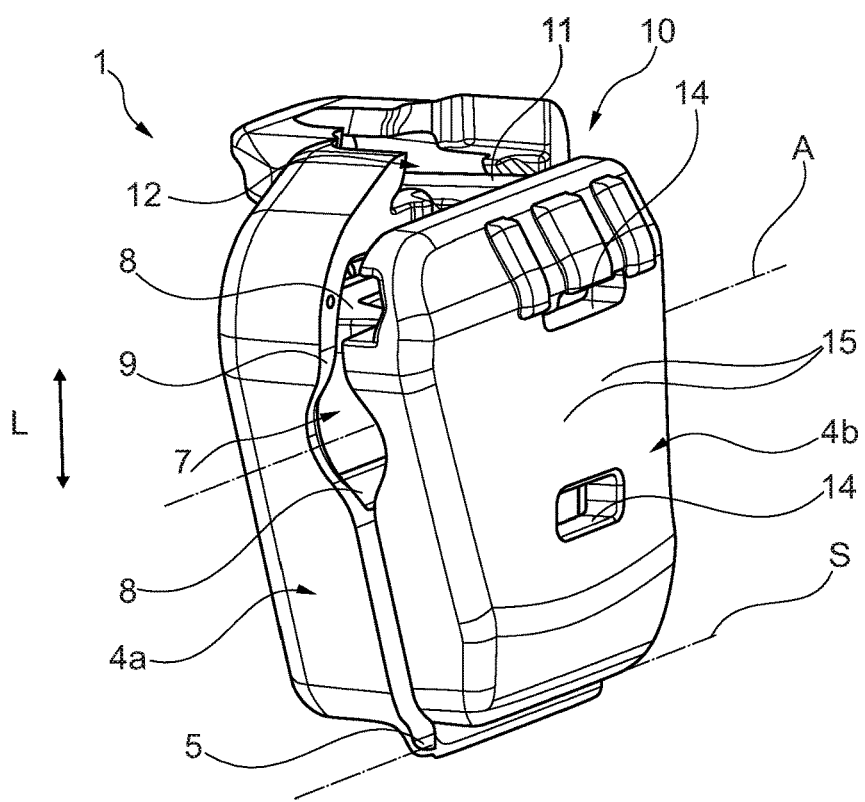
FIG. 5 shows a perspective view of the tube clamp of the first preferred embodiment in a clamping snap-fit position.

FIG. 5 illustrates said clamping snap-fit position of the tube clamp 1 in which the snap hook 11 of the snap-fit closure system 10 is locked and the infusion tube 3 (see FIG. 1) is pinched off.

Figure 6:
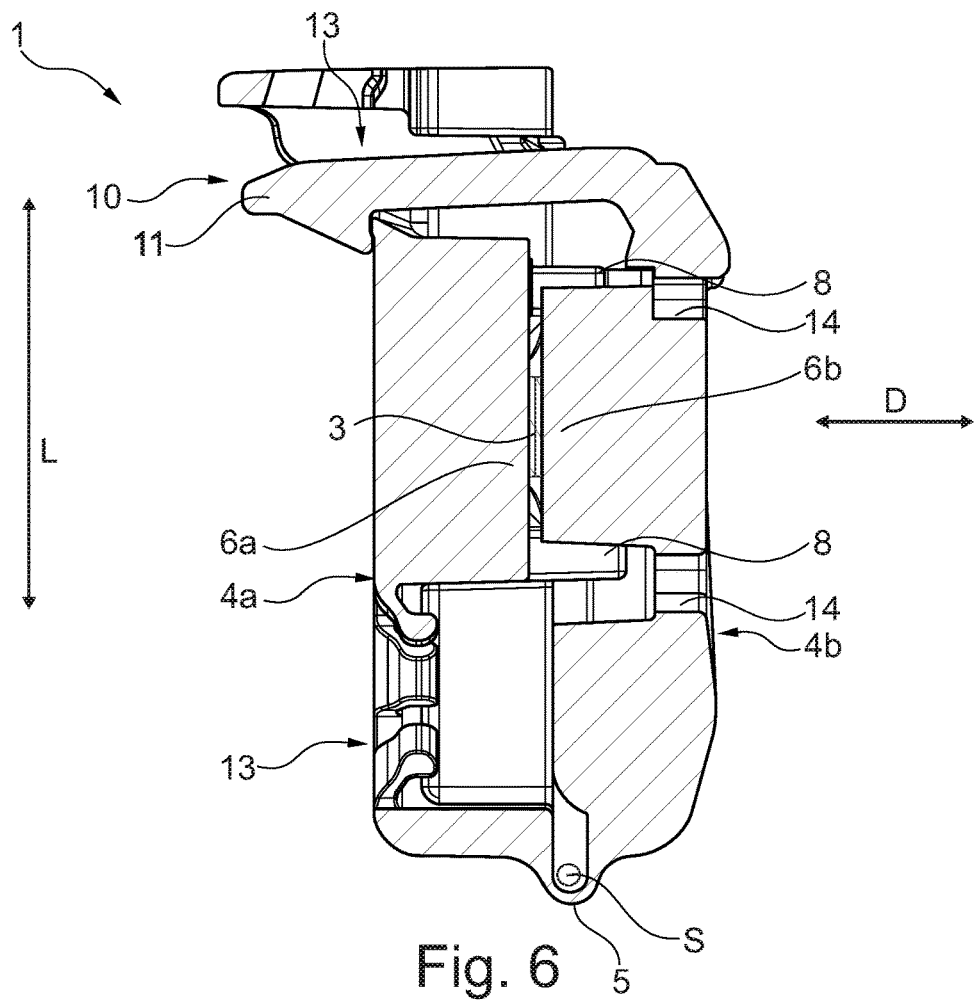
FIG. 6 shows a longitudinal sectional view of the tube clamp of FIG. 5.

In a longitudinal section across the clamping edges 6a and 6b, FIG. 6 illustrates in detail the functioning of the connecting members 15. While the clamping edges 6a and 6b squeeze and pinch off the infusion tube 3 between themselves, the snap hook 11 is locked at the second clamping portion 4b via the undercut. In comparison the two clamping portions 4a, 4b are fixed rigidly against each other with respect to the clamping edges 6a, 6b. Starting from the first clamping edge 6a via the first clamping portion 4a rigidly connected to the first clamping edge 6a, a flux of force extends via two ways, i.e. via the snap-fit closure system 10 (especially snap hook 11) and via the hinge 5 to the second clamping portion 4b and from here (serially) to the second clamping edge 6b while interposing the elastic connecting members 15. Hence in contrast to the state of the art, according to aspects of the invention further elements are interposed in the flux of force, i.e. the connecting members 15, which are structurally effectuated by the two slotted holes 14.

Figure 7:
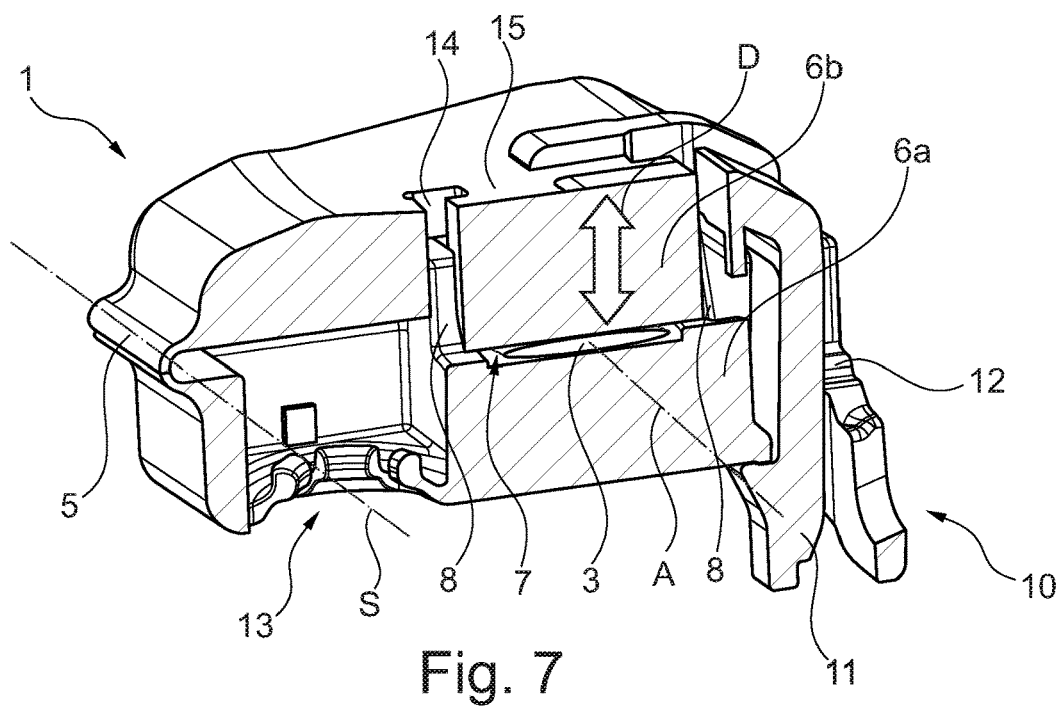
FIG. 7 shows a longitudinal sectional view of a tube clamp according to aspects of the invention of a second preferred embodiment.

FIG. 7 illustrates a tube clamp according to aspects of the invention of a further second preferred embodiment. Here the recesses have a different geometric shape and include, apart from a slotted hole transversely to the longitudinal clamp direction L, also a recess adjacent to the slotted hole in the longitudinal clamp direction L. The shaping the recess allows to further vary and, respectively, define an elasticity of the second clamping edge 6b with respect to the first clamping portion 4b.

It is noted in this context that, instead of the hinge 5 with an accompanying pivoting motion about the pivot axis S, also a translational movement of the two clamping portions 4a, 4b toward each other can be realized, of course. The technical effect of the connecting members 15 and of the elastic coupling again is equal to that as afore-described.

The invention claimed is:

1. A medical tube clamp for clamping a flexible medical tube, comprising:
    a tube receiving area which is adapted to receive the medical tube,
    a first clamping portion including a first clamping jaw movable relative to a second clamping portion including a second clamping jaw, and
    a closure system for safely positioning the first and the second clamping portions in more than one snap-fit position relative to each other so that, when the closure system is unlocked, the medical tube can be inserted in and removed from the medical tube clamp, in an open snap-fit position the inserted medical tube cannot be removed and is not clamped, and in a clamping snap-fit position the medical tube is clamped between the first clamping jaw and the second clamping jaw,
    wherein at least one of the first clamping jaw is configured to be elastically movable relative to a first plate-shaped base of the first clamping portion, the first plate-shaped base having at least one recess in the area abutting on the first clamping jaw, thus causing a first connecting member to be formed in the first plate-shaped base, or the second clamping jaw is configured to be elastically movable relative to a second plate-shaped base of the second clamping portion, the second plate-shaped base having at least one recess in the area abutting on the second clamping jaw, thus causing a second connecting member to be formed in the second plate-shaped base.

2. The medical tube clamp according to claim 1, wherein in the clamping snap-fit position the first clamping portion is positioned rigidly with respect to the second clamping portion by the closure system and at least one of the first clamping jaw or the second clamping jaw is elastically movable substantially in a clamping pressure direction only.

3. The medical tube clamp according to claim 1, wherein the medical tube clamp further includes:
    a hinge, by which the first clamping portion pivots relative to the second clamping portion about a pivot axis so that the medical tube clamp can be opened and closed in a jaw-type manner.

4. The medical tube clamp according to claim 3, wherein the hinge is a film hinge.

5. The medical tube clamp according to claim 1, wherein the medical tube clamp has a mechanism by which the second clamping portion has only one translational degree of freedom and is movable in a direction towards the first clamping portion.

6. The medical tube clamp according to claim 1, wherein the closure system is a snap-fit closure system.

7. The medical tube clamp according to claim 1, wherein the first and second clamping jaws include clamping edges having a longitudinal clamp direction and at least one of the first or second clamping portion has two slotted holes having a longitudinal direction is located transversely to the longitudinal clamp direction and the two slotted holes as the recesses are directly abutting on the respective clamping edge.

8. The medical tube clamp according to claim 1, wherein the connecting member is an elastic material, a spring or a biasing mechanism.

9. The medical tube clamp according to claim 1, wherein the at least one recess is in the form of a slotted hole.

10. A volumetric pump for delivering a fluidal medium through a flexible medical tube, comprising a housing, wherein a medical tube clamp according to claim 1 is fastened on the housing for clamping the medical tube.

11. A medical tube clamp for clamping a flexible medical tube comprising:
    a tube receiving area which is adapted to receive the medical tube,
    a first clamping portion including a first clamping jaw movable relative to a second clamping portion including a second clamping jaw, and
    a closure system for safely positioning the first and the second clamping portions in more than one snap-fit position relative to each other so that, when the closure system is unlocked, the medical tube can be inserted in and removed from the medical tube clamp, in an open snap-fit position the inserted medical tube cannot be removed and is not clamped, and in a clamping snap-fit position the medical tube is clamped between the first clamping jaw and the second clamping jaw,
    wherein at least one of the first clamping jaw is configured to be elastically movable relative to the first clamping portion or the second clamping jaw is configured to be elastically movable relative to the second clamping portion via a connecting member, and
    wherein at least one of the first clamping portion, the connecting member and the first clamping jaw are one piece of material or the second clamping portion, the connecting member and the second clamping jaw are one piece of material.

* * * * *